US007008643B1

(12) United States Patent  (10) Patent No.: US 7,008,643 B1
Hilgers  (45) Date of Patent: Mar. 7, 2006

(54) DELIVERY SYSTEM FOR BIOLOGICAL MATERIAL

(76) Inventor: Arnold Hilgers, Golzheimer Platz 5, 40476 Düsseldorf (DE)

( * ) Notice: Subject to any disclaimer, the term of this patent is extended or adjusted under 35 U.S.C. 154(b) by 0 days.

(21) Appl. No.: 10/018,773

(22) PCT Filed: Jul. 7, 2000

(86) PCT No.: PCT/EP00/06460

§ 371 (c)(1),
(2), (4) Date: Mar. 22, 2002

(87) PCT Pub. No.: WO01/03667

PCT Pub. Date: Jan. 18, 2001

(30) Foreign Application Priority Data

Jul. 8, 1999 (EP) .................................. 99113251
Jan. 20, 2000 (EP) .................................. 00101030

(51) Int. Cl.
A61K 9/14 (2006.01)
A61K 9/16 (2006.01)
A61K 47/30 (2006.01)

(52) U.S. Cl. .................... 424/489; 424/490; 514/772.3
(58) Field of Classification Search ................ 424/489, 424/486, 468, 482; 514/44; 435/455, 320.1
See application file for complete search history.

(56) References Cited

U.S. PATENT DOCUMENTS

| 4,181,589 | A | | 1/1980 | Frosch et al. | |
| 4,849,355 | A | | 7/1989 | Wong | |
| 5,100,591 | A | * | 3/1992 | Leclef et al. | ................. 264/4.6 |
| 5,232,856 | A | | 8/1993 | Firth | |
| 5,609,886 | A | * | 3/1997 | Wantier et al. | ............. 424/497 |
| 5,672,301 | A | * | 9/1997 | Orly et al. | ................... 264/4.1 |
| 5,789,213 | A | * | 8/1998 | Hui et al. | ................... 435/461 |
| 6,183,781 | B1 | * | 2/2001 | Burke | ......................... 424/486 |
| 6,224,794 | B1 | * | 5/2001 | Amsden et al. | .............. 264/4.1 |
| 6,274,175 | B1 | * | 8/2001 | Gombotz et al. | ........... 424/501 |
| 6,291,013 | B1 | * | 9/2001 | Gibson | .................... 427/213.3 |
| 6,303,148 | B1 | * | 10/2001 | Hennink | ..................... 424/489 |
| 6,395,302 | B1 | * | 5/2002 | Hennink | ..................... 424/489 |
| 6,475,779 | B1 | * | 11/2002 | Mathiowitz et al. | ..... 435/320.1 |
| 6,528,035 | B1 | * | 3/2003 | Mathiowitz et al. | ........ 423/407 |
| 2001/0042932 | A1 | * | 11/2001 | Mathiowitz et al. | ......... 264/4.1 |

FOREIGN PATENT DOCUMENTS

EP  0 213 303 A2  3/1987
EP  0 842 657 A1  5/1998

OTHER PUBLICATIONS

US 5,849,884, 12/1998, Woiszwillo et al. (withdrawn)

* cited by examiner

*Primary Examiner*—Dave Trong Nguyen
*Assistant Examiner*—Michael D. Burkhart
(74) *Attorney, Agent, or Firm*—Sughrue Mion, PLLC

(57) ABSTRACT

The present invention relates to a composition and method for delivery of biological material, especially nucleic acids into target cells and into the nucleus.

8 Claims, 1 Drawing Sheet

DELIVERY SYSTEM FOR BIOLOGICAL MATERIAL

FIELD OF THE INVENTION

The present invention relates to a composition and method for delivery of biological material, especially nucleic acids into target cells and/or into the nucleus and claims priority of the European patent application 99 113 251.5 and the European patent application 00 101 030.5 which are hereby fully incorporated in terms of disclosure.

BACKGROUND OF THE INVENTION

The delivery of biological material into cells, especially the delivery of DNA, raises many promising opportunities to treat diseases of both genetic and infectious origin. It is based on delivering biologically active substances such as peptides, proteins or nucleic acids % into somatic cells of an organism in order to influence the cell metabolism or switch off defective genes, to replace a defective gene with an intact gene, or to enable these cells to form a protein that possesses a prophylactic or therapeutic effect.

Examples of genetically caused diseases in which gene therapy represents a promising approach are numerous. Other possible applications are in immune regulation, in which immunity is achieved by the administration of functional nucleic acid codes for a secreted protein antigen or for a non-secreted protein antigen, by immunisation. Other examples of genetic defects in which a nucleic acid which codes for the defective gene can be administered, e.g. in a form individually tailored to the particular requirement, include muscular dystrophy (dystrophin gene), cystic fibrosis (CFTR gene), hyper-holesterolemia (LDL receptor gene). Gene therapy methods of treatment are also potentially of use when hormones, growth factors or proteins with a cytotoxic or immune-modulating activity are to be synthesised in the body.

Gene therapy also appears promising for the treatment of cancer by administering so-called "cancer vaccines". In order to increase the immunogenicity of tumor cells, they are altered to render them either more antigenic or to make them produce certain cytokines in order to trigger an immune response. This is accomplished by transfecting the cells with DNA coding for a cytokine, e.g. IL-2, IL4, IFN gamma, TNF alpha and others. To date, gene transfer into autologous tumor cells has been accomplished via retroviral vectors as therapeutic agents for blocking the expression of certain genes (such as deregulated oncogenes or viral genes) in vivo. It has already been shown that short antisense oligonucleotides can be imported into cells and exert their inhibiting effect therein, even if their intracellular concentration is low, caused by their restricted uptake by the cell membrane as a result of the strong negative charge of the nucleic acids.

Given the substantial benefits that may accrue from the delivery there is a clear need for safe and efficient biological material, mainly nucleic acids, delivery systems.

Various techniques are known for gene transfer into mammalian cells in vitro, e.g. introducing of DNA by means of liposomes, electroporation, microinjection, cell fusion, DEAE-dextran or calcium phosphate precipitation methods. Cationic lipids have been successfully used to transfer DNA. The cationic component of such lipids can compact DNA in solution. This method has been shown to result in heavily aggregated DNA complexes that, when used for transfecting the DNA in vitro, results in increased efficiency of gene transfer and expression (relative to naked DNA). Although the formation of these complexes can promote gene transfer in vitro, the injection of such complexes in vivo does not result in long lasting and efficient gene transfer.

Currently, viruses comprise the most popular vectors for in vitro and in vivo gene delivery. These vectors have been developed to bring about the transfer of genes by using the efficient entry mechanisms of their parent viruses. This strategy was used in the construction of recombinant retroviral and adenoviral vectors in order to achieve a highly efficient gene transfer in vitro and in vivo. For all their efficiency, these vectors are subject to restrictions in terms of the size and construction of the DNA which is transferred and there is a danger that viral coat proteins can trigger immune reactions in the recipient. Furthermore, these agents constitute safety risks in view of the co-transfer of viable viral gene elements of the original virus. Thus, for example, the use of retroviruses is problematic because it involves, at least to a small percentage, the danger of side effects such as infection with the virus (by recombination with endogenous viruses and possible subsequent mutation into pathogenic form) or the formation of cancer. Moreover, the stable transformation of the somatic cells of the patient, as achieved by means of retroviruses, is not desirable in each case because this can only make the treatment more difficult to reverse, e.g. if side effects occur.

Recently, synthetic vectors have been suggested as an alternative to viruses and alternative strategies for gene transfer have been developed.

One example of this is the transfer of genes into the cell via the extremely efficient route of receptor-mediated endocytosis (Ref.1,2). This approach uses bifunctional molecular conjugates which have a DNA binding domain and a domain with specificity for a cell surface receptor. A DNA-binding moiety is usually poly-L-lysine(PLL). Complexes are formed with DNA through electrostatic interactions between the positively charged lysine residues and the negatively charged phosphates in the DNA backbone. The efficiency of gene expression achieved by receptor-mediated endocytosis is affected by a variety of factors, including the diameter of the complexes and the type of targeting ligand used.

There is generally accepted notion that for successful application in vivo the DNA delivery system must be small enough to gain access to target cells. This frequently involves extravasation through endothelia, and the hyperpermeable endothelia associated with tumors have a size restriction of about 70 nm (Ref.3). In addition, most forms of triggered membrane penetration act via the endosomal membrane following endocytosis and pinocytic internalisation is usually limited to materials of less than 100 nm diameter. It has been shown that nucleic acid compaction rather than surface charge was critical for efficient nuclear trafficking(Ref.4).

Given the large size of biomolecules, especially of DNA expression vectors in free solution, it is advantageous for the DNA to be compressed. It is known that DNA can be condensed into polyelectrolyte complexes simply by the addition of polycations such as polylysine (PLL). It is known that conjugates containing higher molecular weight (mw) PLL clearly have on average a larger size and greater polydispersity than those containing lower molecular weight PLL. For example, conjugates based on the largest PLL (224500 Da) show a broad polydispersity of size, ranging up to maximum diameters of 300 nm, while conjugates based on the smallest PLL (3970 DA) show a small size and relatively uniform distribution (diameter ranging from 20–30 nm) (Ref. 5).

Polycations are known to exert a range of non-specific toxicity effects and the concentration of electrostatic charges resulting from polyelectrolyte condensation could yield particles with extremely high charge density and possibly even increased toxicity. The conjugates formed using higher molecular weight PLL show considerably greater cytotoxicity than those formed with the lowest molecular weight polycations (Ref.5).

In DNA-PLL complexes, the function of PLL is to condense DNA into a compact structure. One of the most effective DNA condensing agents is spermine, a tetramine. A peptide analogue of spermine was synthesised to test the premise that short synthetic peptides could in fact function as well or better than PLL. The peptide K8 (Ref.6) is a superior replacement for the high molecular weight PLL. The potential cytotoxicity was compared with that of PLL. K8 is at least 1000-fold less toxic than PLL for HepG2 cells. Similar results were obtained in other cell lines.

Previous studies with DNA-PLL complexes have demonstrated that an endosomal lysis agent is necessary for high efficiency gene transfer. A replication defective adenovirus has been frequently used to achieve levels of expression comparable to recombinant adenovirus containing the same exogenous gene. It is well known that the host immune response to adenovirus limits its use to a single administration. To replace adenovirus as an endosomal lytic agent, fusion peptide of virus protein has been employed. JTS-1, a novel amphipatic peptide has been created (Ref.6). High levels of gene expression were achieved in a variety of cell line's, indicating that DNA-K8/JTS-1 complexes are highly useful for gene delivery in vitro.

The data demonstrate that it is feasible to construct simple DNA-peptide complexes that give high efficiency gene: delivery into cultured cells. These complexes contain only three components: DNA, condensing peptide, and lytic peptide, all of which are molecularly defined and easily undergo self-assembly into an active DNA delivery system. Future development of these complexes holds promise of replacing viral vectors, however, their in vivo application is yet unknown.

Recently (Ref.7) the cationic polymer polyethylenimine (PEI) was shown to mediate efficient gene transfer into a variety of cells without the addition of any cell-binding ligand or endosomolytic moiety. This compound, in contrast to PLL, combines DNA binding and condensing activity with a high pH-buffering capacity. Every third atom of the PEI backbone is protonatable amino nitrogen atom making the polymer an efficient "proton sponge". Endosomal and lysosomal buffering is considered to protect DNA from degradation and to promote release from the acidic vesicles. These properties make PEI a very attractive DNA-binding core for more sophisticated vectors containing cell-binding domains and other cell entry functions. It has been shown that the ligand-PEI conjugates can mediate efficient transfection of cultured tumor cells in a receptor-ligand-dependent manner. This findings indicate that ligand-conjugated PEI might be promising vector for receptor-specific gene delivery (Ref.8).

PEI-DNA complexes with different ratios of PEI nitrogen to DNA phosphate (N/P ratio) have been prepared and tested in a variety of in vivo models. Earlier experiments carried out with the branched 25 kDa PEI show this polymer to be toxic, causing death within a few minutes, even when used at low N/P ratios. Better results are obtainable with linear polymers with a mean molecular weight of 22 kDA (Exgene 500). When complexing a reporter gene (pCMV-Luc) with Exgene 500 at ratios of 3 to 5 (N/P), transgene expression may be found 24 h later in lungs, heart, spleen, liver, kidney and brain (Ref.9). However, toxic and immunogenic characteristics may probably riot be overcome with the use of PEI.

Electroporation, another non-viral delivery system, is used to deliver biological material into target cells by applying an electrical field as described in U.S. Pat. No. 4,849,355; and U.S. Pat. No. 5,232,856. To deliver biological material into cells electric pulses are applied to target cells f.e. in a cell-suspension. The biological material in the suspension may diffuse into the cell through small pores, which are formed in the cell membrane by the application of the electric pulses.

Liposomal techniques have been combined with electroporation techniques to encapsulate the biological materials in liposomes and fuse the liposomes with targeted cells by electrofusion in order to achieve higher efficiency delivery. However, the liposome are weakly loaded and do not fuse well with the target cell in the electrical field.

In the U.S. Pat. No. 5,789,213, fully incorporated by reference, an electroporation system is described that relates to the use of a two phase polymer system that concentrates biological materials with the target cells, such that the materials can be introduced into target cells during and after administration of an electric pulse by concentrating both the target cells, and biological materials to be loaded, into one of the two phases.

A two-phase polymer method is capable of separating or partitioning cells, proteins and minerals (described in U.S. Pat. No. 4,181,589; and Partitioning in Aqueous Two-Phase Systems, 1985, eds., H. Walter, D. Brooks, and D. Fisher, pubis. Academic Press wherein polymer concentrations are % w/w unless-noted otherwise). The partition of particles into different-polymer phases depends on the interfacial energy of the particles and the polymer solutions. By varying the interfacial energy governed by the polymer and salt concentrations, selected particles (cells, macromolecules) can be driven into a given phase, hence achieving the purpose of separation or partitioning by the use of combinations of polymers.

According, to U.S. Pat. No. 5,789,213 a composition is used which functions to concentrate both target cells and biological materials into a single phase, and function to reduce the volume of this phase by osmotic control so that cells and biological materials are encapsulated in this single phase in a concentrated form during electroporation. Biological materials are then driven into the target cells during electroporation, and subsequent colloidal-osmotic swelling of cells after electroporation is limited, result in a higher loading efficiency. For example a two-phase polymer system using polyethylene glycol (PEG; molecular size (m.w,) 8,000 (in daltons)) and one of three formulations of dextran (dx; m.w. 9,000, and 71,000 and 249,000) is described.

However, electroporation beyond other disadvantages requires special equipment and is limited to use in vitro.

Delivery of bioactive molecules such as nucleic acid can be significantly enhanced by immobilisation of the bioactive molecule in a polymer microparticles which facilitates transfer of the molecule into the targeted areas as described above. However, polymers preferably must be non-toxic, containing no toxic monomers and degrading into non-toxic components, be biocompatible, be chemically compatible with the substances to be delivered. To make microparticles from synthetic and natural polymers a number of different techniques have been developed.

In the U.S. Pat. No. 5,849,884, fully incorporated by reference, macromolecular microparticles and a method of production and use are described. This method is based on the collapse of macromolecules with a tertiary or quaternary structure, forming the basic structure: elements. Microparticles are produced by mixing macromolecules in solution or a liquid phase with a polymer or mixture of polymers in solution or a liquid phase in the presence of an energy source for a sufficient amount of time to form particles. The solution is preferably an aqueous solution. Either the macromolecule solution is added to the polymer or the polymer solution is added to the macromolecule solution to cause removal of water from, or dehydration of the macromolecules. This process is also referred to by those skilled in the art as "volume exclusion".

The types of macromolecules forming the microparticles include proteins, peptides, carbohydrates, conjugates, nucleic acids, viruses, or mixtures thereof. Since macromolecules are the major structure forming elements within the microparticles suitable macromolecules need to have or to be capable of having a tertiary or quaternary structure. The preferred polymer is polyvinylpyrrolidone (PVP), polyethylene glycol (PEG), dextran (Dx), polyoxyethylene-polyoxypropylene copolymer (PPC), polyvinyl alcohol (PVA), or mixtures thereof.

Each microparticle is composed of at least 40% by weight macromolecules and less or equal than 30% by weight polymer molecules, which are intertwined or interspersed in the microparticle and are generally homogeneously distributed.

In order to induce the microparticles forming collapse of the macromolecules the macromolecule-polymer solution is incubated in the presence of an energy source for a predetermined length of time. The preferred energy source is heat. However, possible energy sources include heat, radiation, and ionisation, alone or in combination with sonification, vortexing, mixing or stirring. Preferably, the macromolecule-polymer solution mixture is incubated in a water bath at a temperature greater than or equal to 37° C. and less than or equal 90° C. for between approximately 5 minutes and 2 hours. Most preferably, the mixture is incubated for 5–30 minutes at a temperature between 50 and 90° C.

This method needs the macromolecule-polymer solution to be adjusted to a certain pH range, either before, after or during the mixing of the polymer with the macromolecule, to a pH near the isoelectric point (pI) of the macromolecule, preferably within 3 to 4 pH units of the pI of the macromolecule; most preferably within 1.5 to 2 pH units of the pI of the macromolecule.

Microparticles composed of nucleic acids have to be prepared by first mixing the nucleic acid either with a protein, such as bovine serum albumin, or, because nucleic acids are anions, the addition of a cation, such as poly-L-lysine (PLL), which aids greatly in the formation of microparticles.

In respect to this composition it is disadvantageous, that the method is limited to a certain pH range of the macromolecule polymer solution. Additionally, it requires a special equipment in order to incubate the solution with energy, for example heating, in combination with stirring, vortexing or mixing.

Further more, it is limited to macromolecules having or capable of having a tertiary or quaternary structure.

Most of all, this method does not solve the difficulties related to the transfer of genes into cells of an organism. In particular, the problems related to the penetration of biological material, especially nucleic acid, into cells and their nuclei are not solved.

SUMMARY OF THE INVENTION

It is therefore an object of the invention, to provide an efficient in vitro and in vivo delivery system for biological material, especially for polynucleotides.

The invention is based on the finding, that, under certain conditions, an aqueous polymer solution will spontaneously separate into a two phase polymer system. During this process H bonds between uncharged polymers molecules can be formed. Also H-bond formation can take place when a macromolecule is charged. Simultaneously, a spontaneous increase in concentration of biological material and polymer occurs in one of the phases which subsequently leads to the formation of microparticles with high transfection properties which can be used to introduce genes into a number of organs in vivo.

The microparticles formed by the method according to the invention can be composed of polymer molecules of at least 75% and biological material of 25% or less. The polymer molecules can be the major structure forming element.

These microparticles penetrate into all types of cells and nuclei which can be proven by fluorescent microscopy.

A better understanding of the features of the present invention will be obtained from the following description of preferred embodiments and examples (see also FIG. 1).

DETAILED DESCRIPTION OF THE INVENTION

Figure 1:
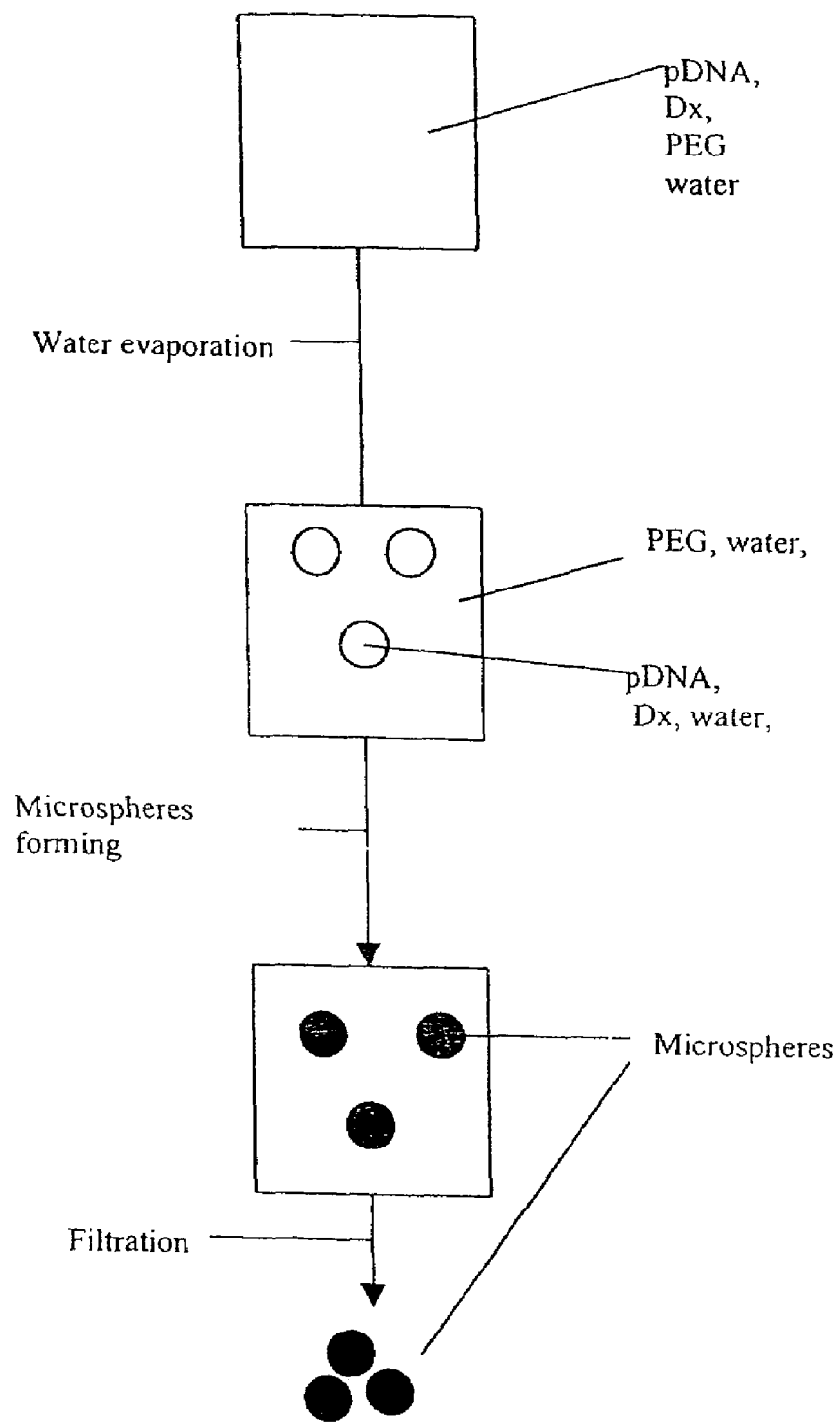
FIG. 1 is a flow diagram for the preparation of microspheres.

A two-phase polymer method is capable of separating or partitioning cells, proteins and minerals (described in U.S. Pat. No. 4,181,589). The partition of particles into different polymer phases as explained depends on the inter-facial energy of the particles and the polymer solutions. By varying the inter-facial energy governed by the polymer and salt concentrations, selected particles (cells, macromolecules) can be driven into a given phase, hence achieving the purpose of separation or partitioning by the use of combinations of polymers (Ref.10).

A spontaneous phase separation is achieved when the water is partially evaporated from the one-phase polymer1 (P1)-polymer2(P2)-macromolecule (e.g. nucleic acid or protein) water system and two aqueous phases are formed, in form of the water in water mixture (W1/W2; W1-dispersed phase, W2-continuous phase). The process is promoted by decreasing temperature. It can even be conducted at a temperature of approximately 0° C.

The first phase consists of water and mainly P1, the second phase consists of water and mainly P2. The partition coefficient of a macromolecule can always be adjusted to move it exclusively into one of the two phases. When macromolecule is a nucleic acid, one-phase Dx-PEG-nucleic acid-water system is preferable. Microparticles with high transfection properties are formed when nucleic acid is concentrated in Dx-phase.

When the W1 phase is forming (during the evaporation process), a high concentration of carbohydrates and biological material in particles of the discontinous phase occurs and hydrogen bonds formation between polymer molecules acts mainly as a stabilising phenomenon for microparticles structure. (Ref.11).

Dextran is the best polymer for microparticles formation because this polymer is biodegradable and has been used as a plasma expander for a long period of time. Moreover, a number of formulation for controlled release and drug targeting are based on the utilisation of dextran or its derivatives or analogies (Ref.11).

Besides dextran, suitable polymers include other carbohydrate-based polymers, such as methylcellulose, chitin or starch. Also polyalipathic alcohols such as polyethylene oxide and derivates thereof, e.g. polyethylene glycol (PEG) or PEG-acylate and poly(vinyl) polymers and derivates thereof, such as poly(vinyl)alcohols may be suitable. Also polyaminoacids, such as polylysine, can be used. Further more the inventive compositioin can comprise naturally occurring polymers, such as zein, pullulan, or chitosan or derivates thereof as components of the aqueous polymer system.

The biological material being comprised by the composition according to the invention can include all substances of natural or synthetic origin. Preferably these substances show a biological activity within or at the target cell. It is advantageous, that the biological material is not limited to macromolecules with a tertiary or quaternary structure.

Thus, the microparticles formed by the composition can include peptides, proteins, enzymes, recombinant proteins nucleic aids, hormones, growth factors, carbohydrates, lipids, and derivates thereof. Also viruses, virus particles or plasmids can be mixed with the polymers as mentioned above in order to form microparticles. Small molecules, such as a hapten, can be conjugated to macromolecules, e.g. to a protein, before being added to the polymer solution. An organic or inorganic pharmaceutical compound or drug my be incorporated into the microparticle by attaching the drug to a macro-molecule, such as a protein. Subsequently, the microparticles can be formed with the macromolecule-drug complex or conjugate.

It is understood, that the term biological materials encompasses also a combinations of the substances mentioned above. The term also comprises bio-logically active material, as well as material of biological origin.

The nucleic acid microparticles may as well include pharmaceutical substances, such as chloroquine, which allows nucleic acids to escape from cytoplasmic compartments into the cytoplasm so that it can be more easily transcribed and translated by the cells.

In order to support cancer therapy the microparticles forming composition can comprise growth regulating factors such as interleukine or interferone.

Additionally, the microparticles may be coated with substances that increase the efficiency of translation, or may be coated with substances, such as surfactants as Tween, to support and provide cell-specific targeting of microparticles.

In a preferred embodiment, the composition according to the invention comprises a nucleic acid binding agent, such as polylysine or polyethylenimine (PEI). The use of a binding agents with condensing activities, e.g. tetramine such as spermine, can be advantageous. The condensing agent can be connected to one or more additional vector(s) or ligand(s).

Further more, the condensing agent can be advantageously combined with a lysis agent, for example lytic peptides, in order to improve the efficiency of gene transfer. As a lysis agent a replication defective adenovirus or fusion peptides of virus proteins can be employed.

The invention can be used to form vehicles for gene therapy or the production of "genetic vaccines" when the composition comprises nucleic acids, such as DNA or RNA.

The nucleic acids loaded microparticles can be delivered to target cells, for example to mammalian cells, in much the same way as naked DNA is delivered. The delivery in vitro, for example to cells being part of a tissue culture, is also possible.

A delivery system according to the invention can be applied to target cells of various types of organisms. Preferably, it is used for target cells of mammals in vitro and in vivo, especially of human cells. Nevertheless, also cells of lower animals, such as amphibia or reptilia, can be targeted. Besides, applying this method biological material can be delivered into protoplasts of plant cells and into microorganisms.

With respect to mammalian target cells in vivo, especially to humans, the microparticles can be administered to a patient intravenously, intramuscularly, or subcutaneously or in other known ways appropriate to the therapeutic effect desired, including as an aerosol or spray for lungs or by direct lavage through orifices. The microparticles can be lyophilised and then formulated into an aqueous suspension in a range of microgram/ml to 100 mg/ml prior to use. They can be administered once, or may be divided into a number of small doses to be administered at varying intervals of time, depending on the desired dosage.

Definitions:

Delivery system refers generally to a vehicle and mechanism enabling the transport of synthetic or natural substances into a target cell. A delivery system may have various compositions and origins. Well known examples are liposomes, polymer conjugates and viruses. Often, they are used to deliver biologically active substances to and into target cells.

Target cell refers to cells, tissue, organisms, organs or organells which are the destination of substances transferred by delivery systems. They represents either the living organism itself, cells, tissue, organs or organells within a living organism or a cell culture or form a part thereof. The biological material can be connected to ligands which are constituted by biological material as defined above.

Biological material refers to substances of natural or synthetic origin, which preferably show a biological activity within or at the target cell. Biological material include peptides, proteins, enzymes, recombinant proteins nucleic aids, hormones, growth factors, carbohydrates, lipids, viruses or virus particles, plasmids, antibodies or derivates, combinations or polymers thereof.

Microparticles refer to solid or semi-solid particles having a diameter preferably less than one millimeter, more specifically less than 100 micrometer, which can be formed of a variety of materials, including synthetic polymers, proteins and polysaccharides. Microparticles also refer to microcapsules and microspheres.

Nucleic acid-binding agent refers to natural or synthetic substances forming complexes with nucleic acids or comparable material. Preferably they comprise polycations which constitute electrostatic interactions between their positive charge residues and the negatively charged phosphate backbone of nucleic acids. They can provide additionally condensing and/or buffering activity.

Surfactant refers to substances or natural or synthetic origins which are integrated into the microparticle forming composition or are coating the microparticels. Preferably they comprise hydrophilic and liphophilic substances.

EXAMPLES

The invention is further described by examples of preferred embodiments.

Example 1

1.1 Fluoresceinylated Proteins

Proteins were fluoresceinylated by using fluorescein isothiocyanate (FITC). To remove any trace of free fluorescein, fluoresceinated proteins were precipitated by ethanol, pelleted by centrifugation, and then dissolved in PBS.

1.2 Fluoresceinylated Polymers

FD-20S, FD-70S, FD-500S (FITC-labelled dextrans) were purchased from Sigma Chemical Company (St. Louis, Mo. USA) and used for detection of intracellular microparticles localisation.

1.3 Derivatives of Dextrans

Procedures of attachments of DNA-binding and biologically active proteins and peptides to dextrans are described in detail and well known to those skilled in the art (see for example Roger L. Lundblad, "Techniques in Protein Modification", 1995).

1.4 Cells

Cells can be purchased from the American Type Culture Collection (ATCC, Rockville, Md., USA). Cells are cultured according to recommendations in the literature. In general, they are maintained in Dulbecco's modified Eagle's medium (DMEM) supplemented with 10–20% fetal calf serum, penicillin (100U/ml), streptomycin (100.mu.g/ml) and 2 mm L-glutamine (GIBCO, Gaithersburg, Md., USA).

1.5 Polymers

Dextrans, polyethylenglycols, poloyvinylpyrrolidones and other (co)polymers are commercially available from chemical suppliers such as the "Sigma" (USA), the "Serva" (Germany), the "Fluka" (Switzerland).

1.6 Preparation of Microparticles

One-phase aqueous solutions containing dextran (P1; 20–500 kDa; Serva) and PEG (P2, 1.5–35 kDa; Serva) or PVP (P2, 10–360 kDa, Fluka) or Tween-80 (P2; Serva) or Pluronic F-68 (P2; Serva) or Ficoll (P2; Serva) are prepared. Then the FITC-labelled Dx (FD-20, 70, 500S, Sigma Chemical Company, St. Luis, Mo., USA) or FITC-labelled protein is added and the evaporation process is started. After 5–10 hours; the evaporating process is stopped. Afterwards, P2 can be removed in accordance with the methods known to the skilled person. Microparticles are frozen and dried for storage. The mean diameter of the microparticles varys between 0.03 and 3 microns, the particle size is dependent on the P1 phase/P2 phase volume ratio of the W1/W2 emulsion, polymer molecular weights, their nature, temperature and evaporating rates.

The size of microparticles which is suitable for intracellular delivery was determined by means of photon correlation spectroscopy (Zeta sizer 1, AZ 110, 90 degree, wavelength 633). The size is adjusted to 200–300 nm by varying: P1/P2 (w/w) ratio in aqueous one-phase solutions (R1); R1=0.01–1.0;
evaporating process duration (D, hours); D=5–10;
temperature(T.gradee.C); T=25,37;

1.7 In vitro Experiment

Human hepatocarcinoma cells (HepG2 cells; ATCC HB-8065, ATCC, Rockville, Mass., USA) are cultured in Dulbecco's Modified Eagle Medium (DMEM) containing 10% heat-inactivated serum. Medium and fetal bovine serum (FBS) are from GIBCO-BRL (Gaithersburg, Md., USA). Culture media are supplemented with 2 mM L-glutamine and antibiotics (100 units/ml penicilin and 0.1 mg/ml streptomycin; GIBCO).

HepG2 cells are plated in 24-well plates the day before transfection. Cells are transfected in a final volume of 0.75 ml per well of culture medium containing 2 mg microparticles. The size of microparticles is 0.2–0.3 microns. The microparticles consist of Dx (20, 70, 500 kDa) and Dx (FD-70S, 500S; 2.mu.g) or FITC-labelled HSA (human serum albumin; 2.mu.g). After 6 or 24 h incubation at 37° C., the transfection medium is removed and the cells are washed in PBS containing BSA and fixed for 30 minutes in 5% acetic acid in methanol at −20° C.

Experiments are carried out several times with 3T3 fibroblast and also with HeLa cells. Within a series, experiments are done in duplicate. Intact cells were used as control.

Fluorescent microscopy then reveals intranuclear and intracellular localisation of microparticles in all types of cells used.

Example 2

2.1 Preparation Microparticles for Transfection

One-phase aqueous solutions containing of Dx (P1; 20,70,500 kDa; Serva), PEG (P2; 6 kDa; Serva) or PVP (P2; 40 kDa; Fluka) or Ficoll (P2; Serva) or Pluronic F68 or Tween 80 and polynucleotide in form of plasmid containing the coding sequence of beta-galactosidase (LacZ) under the CMV promoter (Clonetech, Palo Alto, Calif., USA) are prepared and then the evaporation process is conducted (see Example 1).

The size of the particles is adjusted to 100–200 nm by varying R1, D and T. The including grades are appreciated by means of agarose gel electrophoresis (1% agarose gel, TAE buffer, pH 7.4, 90V, 3 h). Unincluding plasmid is detected by ethidium bromide intercalation. A plasmid DNA including grade of 0,95 are achievable without use of DNA-binding agent such as PLL when P1/pDNA, w/w, ratio is more than 25. In other cases, polycations such as PLL, peptides or dextrans substituted by a DNA-binding agents are used.

2.2 In vitro Transfection

Cells are plated 24 h before the experiment on 24-well tissue culture plates and transfected (see Ex.1). After 24 h incubation at 37° C., the transfection medium is removed, the cells are washed in PBS containing BSA and fixed for 30 minutes in 5% acetic acid in methanol at −20° C. and exposed to X-gal solution overnight at 37° C. After staining, LacZ expression is found in all types of cells used (HeLa, 3T3,HepG2).

2.3 In vivo Transfection

Mice are injected through the tail vein with microparticles (Dx/pCMV LacZ 2.5 mg/0.025 mg per animal) in 0.1 ml of 150 mM NaCl saline solution. The mice were sacrificed two weeks after the injection and sequentially perfused with 5 mg/l heparine in saline, 4% paraformaldehyde in PBS and a standard β-galactosidase revealing solution (1 mg/ml X-gal; Sigma). After perfusion, all the organs were dissected and B-galactosidase revelation was continued for 48 hours by immersion in the X-gal solution at 30.gradee C. After staining, the organs were embedded in parafin for histochemistry. Transgene (LacZ) expression was found in lungs, heart, muscles, liver and brain.

Example 3

3.1. Biological Material:

As biological material pCMVLacZ containing bacterial β-galactosidase driven by a human cytomegalovirus promoter or pNTβGal, which is a similar construct modified by a signal of nuclear localization, is comprised within the composition.

3.2. Preparation of Microparticles

The microparticles are prepared as described in detail under examples 1 and 2.

3.3. Microparticle Characterization

The size distribution of the microparticles is determined by using electron microscopy. All particles have a diameters of approximately 1 micron.

3.4 In vivo Transfection

Gene transfer is carried out on mice. For the administration of microparticles intramuscular (musculus quadriceps f.) and intravenous (tail vein) routes are used. 25 or 50 μg of plasmid DNA are loaded in microparticles for each injection. Control animals are transfected with the same amount of naked plasmid DNA.

3.5. Animals Scarification

Animals scarification was on day 14 after administration.

3.6. β-Gal Expression Analysis

In case of intramuscular administration tissue samples of the injected muscle, liver or lung are taken. In case of intraveneous administration tissue samples are taken from liver or lunge. None of this tissue samples exhibit any signs of tissues degeneration.

3.7. Transgene Expression Examination

After scarification tissue samples are snap-frozen in liquid nitrogen and processed for subsequent qualitative cytochemical marker gene expression examination on cryostat sections or on the whole organ samples.

The proportion of β-Gal positives cells (nuclei) to the total number of cells (nuclei) is quantified as a mean for the transfection efficiency:

After intramuscular injections the proportion of positive cells was 0.01–0.07 in muscle tissue and 0.01–0.03 in liver and lung tissue.

After intravenous injections proportion of positive cells was 0.01–0.05 both, i.e. in liver and lung.

Whereas the invention is described in detail, examples are included for illustration. Modifications of the present invention that are obvious to the man skilled in the art are intended to be within the scope of the patent claims.

For reasons of disclosure the following documents are fully incorporated by reference herewith.

REFERENCES

1. Wu, George Y. et al. "Receptor-mediated Gene Delivery and Expression in Vivo." The Journal of Biological Chemistry, vol. 263 No. 29, pp. 14621–14624. Oct. 15, 1988.
2. Wu, George Y. et al. "Receptor-mediated Gene Delivery in Vivo." The Journal of Biological Chemistry, vol. 266 No. 22, pp. 14338–14342. Aug. 5, 1991
3. Seymour, L. W.; "Passive tumor targeting of soluble macromolecules and drug conjugates", Crit. Rev. Ther. Drug Carriers Syst., 1992, V.9, p. 135–137;
4. Pollard H. et al; "Polyethylenimine but not cationic lipids promotes transgene delivery to the nucleus in mammalian cells"; The Journal of Biol. Chem., 1998, V. 273, N13, p. 7507–7511;
5. Wolfert, M. A., Seymour, L. W.; "Atomic force microscopic analysis of the influence of the molecular weight of PLL on the size of polyelectrolyte complexes formed with DNA"; Gene Therapy, 1996, V.3, p. 269–273;
6. Gottschalk, S. et al.; "A novel DNA—peptide complex for efficient gene transfer and expression in mammalian cells"; Gene Therapy, 1996, V.3, p. 448–457;
7. Boussif O. et al, "A novel versatile vector for gene and oligonucleotide transfer into cells in culture and In vivo: polyethylenimine"; PNAS USA, 1995, V. 92, p. 7297–7303;
8. Kircheis, R. et al. "Coupling of cell-binding ligands to polyethylenimine for targeted gene delivery"; Gene Therapy, 1997, V.4,p. 409–418;
9. Goula, D. et al; "Polyethylenimine-based intravenous delivery of transgenes to mouse lung"; Gene Therapy, 1998, V. 5. p. 1291–1295;
10. Partitioning in Aqueous Two-Phase Systems, 1985, eds., H. Walter, D. Brooks, and D. Fisher, Academic Press
11. Schröder, U.; "Crystallised carbohydrate spheres for slow release and targeting"; Method in enzymology, 1985, V. 112, p. 116–128;
12. Franssen, O., Stenekes, R. J., Hennink, W. E.; "Controlled release of a model protein from enzymatically degrading dextran microspheres", J. Controlled Release, 1999 May 20; 59(2), p. 219–228;

REFERENCES FOR ALTERNATIVE MICROENCAPSULATION TECHNIQUES

1. Schröder, U.; "Crystallised Carbohydrate Spheres for Slow Release and Targeting"; 1985, Methods in Enzymology, V.112, p. 116–128;
2. Stenekes, R. J., Franssen, 0. et al.; "The use of aqueous PEG/dextran phase separation for the preparation of dextran microspheres", Int. J. Pharm. 1999 Jun. 10; 183 (1), p. 29–32;

REFERENCES FOR NON-TOXICITY OF DEXTRAN

1. Reza Mehvar, Megan A. Robinson, James M. Reynolds, "Molecular Weight Dependent Tissue Accumulation of Dextrans: In Vivo Studies in Rats"; Journal of Pharm. Sciences, 1994, V.83, No.10, p. 1495–1499;
2. Thoren, L., Develop. Biol. Stand., 1981, 48, 157–167;
3. Yamaoka, T., Tabata, Y; Ikada, Y.; Drug Delivery, 1993, V. 1, p. 75–82;

What is claimed is:

1. A method for the preparation of microparticles from a liquid one-phase system containing biological material and a suitable amount of at least two compounds being incompatible in aqueous solution, the method consisting of the method step of evaporating water from the one-phase system leading to a phase separation with a dispersed phase and a continuous phase, thereby producing the formation of the microparticles, wherein the first compound of the at least two compounds is a dextran-based polymer, and the second compound of the at least two compounds is a polyaliphatic alcohol or derivative thereof, and wherein the evaporating step does not employ any emulsification means, vortexing step, or stirring step.

2. The method according to claim 1, wherein said evaporating step has a duration between 0.1 and 100 hours.

3. The method according to claim 1, wherein said evaporating step has a duration between 0.1 and 50 hours.

4. The method according to claim 1, wherein said evaporating step is carried out at a temperature between 0° C. and 100° C.

5. The method according to claim 1, wherein said evaporating step is carried out at a temperature between 0° C. and 50° C.

6. The method according to claim 1, wherein said evaporating step is carried out under a pressure of 0.1 to 760 mm Hg p.

7. The method according to claim 1, wherein said evaporating step is stopped when the water concentration within the system is between 5 to 80%.

8. The method according to claim 1, wherein said evaporating step is stopped when the water concentration within the system is between 5 to 75%.

* * * * *